(12) United States Patent
Won

(10) Patent No.: US 10,321,826 B2
(45) Date of Patent: Jun. 18, 2019

(54) OPTICAL DYNAMIC IMAGING SYSTEM

(71) Applicant: TEMPLE UNIVERSITY—OF THE COMMONWEALTH SYSTEM OF HIGHER EDUCATION, Philadelphia, PA (US)

(72) Inventor: Chang-Hee Won, Maple Glen, PA (US)

(73) Assignee: TEMPLE UNIVERSITY—Of The Commonwealth System of Higher Education, Philadelphia, PA (US)

(*) Notice: Subject to any disclaimer, the term of this patent is extended or adjusted under 35 U.S.C. 154(b) by 204 days.

(21) Appl. No.: 15/261,032

(22) Filed: Sep. 9, 2016

(65) Prior Publication Data

US 2017/0078584 A1    Mar. 16, 2017

Related U.S. Application Data

(60) Provisional application No. 62/216,491, filed on Sep. 10, 2015.

(51) Int. Cl.
*A61B 5/00*    (2006.01)
*H04N 5/33*    (2006.01)
(Continued)

(52) U.S. Cl.
CPC .......... *A61B 5/0075* (2013.01); *A61B 5/0053* (2013.01); *A61B 5/0064* (2013.01);
(Continued)

(58) Field of Classification Search
CPC .... G01B 11/02; G01B 5/0075; G01B 5/0064; G01B 5/0091
See application file for complete search history.

(56) References Cited

U.S. PATENT DOCUMENTS 6,218,673 B1 * 4/2001 Gore .................. G01N 21/4795
                                                250/473.1
6,264,610 B1    7/2001 Zhu
(Continued)

FOREIGN PATENT DOCUMENTS

WO    2012006431 A2    1/2012

OTHER PUBLICATIONS

Hosseini, et al., "A medical tactile sensing instrument for detecting embedded objects, with specification application for breast examination", The International Journal of Medical Robotics and Computer Assisted Surgery, 2010; 6: 73-82.
(Continued)

*Primary Examiner* — Dominic J Bologna
(74) *Attorney, Agent, or Firm* — Drinker Biddle & Reath LLP

(57) ABSTRACT

The dynamic positioning of sensors, which exploit the mechanical and physiological changes in tissues, can significantly increase the performance in characterization of tumors. Here, we disclose the Optical Dynamic Imaging (ODI) System for tumor characterization. ODI System estimates size, depth, elastic modulus and optical properties of embedded objects. The ODI System consists of a tactile imaging sensor (TIS), and a near infrared diffuse spectral imaging. To obtain mechanical properties of the target, we compress the region of interest with the probe, then the light from the probe is scattered and captured by the camera as a tactile image. On the other hand, using a light source and the camera as a detector, we obtain the diffuse spectral images. From these images, we compute the absorption coefficient of the embedded tumor phantom. We move the source-detector simultaneously and collect optical information. We termed this maneuver as dynamic positioning. Optical Dynamic Imaging System also provides position and orientation of the
(Continued)

light source and the detectors. The combination of the absorption coefficient and tactile data along with location information improves the size, depth, and elastic modulus estimation.

32 Claims, 3 Drawing Sheets

(51) Int. Cl.
G01B 11/02 (2006.01)
G01B 11/14 (2006.01)
G01B 11/22 (2006.01)
H04N 5/225 (2006.01)
H04N 5/232 (2006.01)
H04N 5/235 (2006.01)

(52) U.S. Cl.
CPC ............ *A61B 5/0077* (2013.01); *A61B 5/442* (2013.01); *A61B 5/444* (2013.01); *G01B 11/02* (2013.01); *G01B 11/14* (2013.01); *G01B 11/22* (2013.01); *H04N 5/2256* (2013.01); *H04N 5/232* (2013.01); *H04N 5/2351* (2013.01); *H04N 5/33* (2013.01); *H04N 5/332* (2013.01); *A61B 5/0091* (2013.01); *A61B 2562/0233* (2013.01); *A61B 2562/0238* (2013.01); *A61B 2576/00* (2013.01)

(56) References Cited

U.S. PATENT DOCUMENTS

| | | | |
|---|---|---|---|
| 2003/0164954 A1* | 9/2003 | Gerhard | A43D 1/025 356/635 |
| 2006/0152885 A1 | 7/2006 | Hewit et al. | |
| 2006/0173319 A1 | 8/2006 | Sumi | |
| 2007/0213617 A1 | 9/2007 | Berman et al. | |
| 2008/0179507 A2 | 7/2008 | Han | |
| 2008/0284925 A1* | 11/2008 | Han | G06F 3/0425 349/12 |
| 2010/0103137 A1 | 4/2010 | Ciesla et al. | |
| 2013/0070074 A1* | 3/2013 | Won | G01L 1/247 348/77 |
| 2015/0065821 A1* | 3/2015 | Conrad | A61N 2/004 600/309 |
| 2016/0228008 A1 | 8/2016 | Lee | |

OTHER PUBLICATIONS

Lee, et al., "High Resolution Tactile Imaging Sensor using Total Internal Reflection and Non-rigid Pattern Matching Algorithm", Sensors Journal, IEEE 11(9): 284-2093 (published on-line Jan. 28, 2011).

Lee, et al., "Design and Evaluation of an Optical Tactile Imaging Device for Tumor Detection", 52nd Annual Meeting of American Association of Physicists and Medicine (AAPM), Philadelphia, PA, Jul. 18-22, 2010.

Lee, et al., "Tactile sensation imaging for artificial palpation", Eurohaptics Jul. 8-10, 2010, Amsterdam.

Lee, et al., "Tactile Imaging Sensor for Subsurface Tumor Detection in Prostate Phantom", The First AMA-IEEE Medical Technology Conference on Individualized Healthcare, Washington, DC, Mar. 21-23, 2010.

Lee, et al., "Tactile sensation imaging system for inclusion characterization", Proc. SPIE 7890, Advanced Biomedical and Clinical Diagnostic Systems IX, 78901D (Feb. 21, 2011).

Lee, et al., "Design and Evaluation of an Optical Tactile Imaging Device for Tumor Detection", Abstract ID13673, 52nd Annual AAPM Meeting (Jul. 18, 2010).

Ohka, et al., "An Experimental Optical Three-axis Tactile Sensor Featured with Hemispherical Surface", Trans. Jpn. Soc. Mech. Eng., vol. 74, No. 742, C (2008), pp. 1477-1484.

Shen, et al., "Quantification and Verification of Automobile Interior Textures by a High Performance Tactile-Haptic Interface", Proceedings of the 2006 IEEE/RSJ, International Conference on Intelligent Robots and Systems, Oct. 9-15, 2006, Beijing, China.

Zhang, et al., A Multi-Purpose Tactile Sensor Inspired by Human Finger for Texture and Tissue Stiffness Detection, Proceedings of the 2006 IEEE International Conference on Robotics and Biomimetics, Dec. 17-20, 2006, Kunming, China.

* cited by examiner

OPTICAL DYNAMIC IMAGING SYSTEM

CROSS-REFERENCE TO RELATED APPLICATION

This application claims benefit of U.S. Provisional Patent Application No. 62/216,491 for an "Optical Dynamic Imaging System," filed on Sep. 10, 2015, the disclosure of which application is incorporated herein by reference in its entirety as though explicitly set forth. This application is related to International Patent Application No. PCT/US 2011/043203, filed by the present inventor on 7 Jul. 2011, published as WO 2012/006431 on 12 Jan. 2012, and now also pending as U.S. patent application Ser. No. 13/702,042, published as US 2013/0070074 on 21 Mar. 2013. The disclosure of that application is incorporated herein by reference in its entirety as though explicitly set forth.

FIELD OF THE APPLICATION

The application relates to dynamic optical detection and measurement of an at least partially opaque target, and especially a tumor or other solid inclusion within a larger solid body.

BACKGROUND

Any form of invasive examination of the human body presents risks, and requires considerable resources. Assessment of tumors by non-invasive techniques, in order to determine whether a biopsy or surgical removal of the tumor is necessary, is therefore highly desirable.

In our above mentioned previous WO 2012/006431, we describe a Tactile Imaging System that images the size and shape of a tumor or other subsurface inclusion in a solid body by pressing a flexible waveguide against the surface of the body. Light is propagated through the waveguide by total internal reflection (TIR). Distortion of the waveguide by the inclusion breaks TIR, and the escaping light is imaged. The resulting image provides valuable information on the size and shape of the tumor, and if different images are taken at different contact pressures, valuable information can also be extracted regarding the elasticity of the tumor.

In Sahu et al., "Tactile and Hyperspectral Imaging Sensors for Mammary Tumor Characterization," Proceedings of IEEE Sensors Conference, Baltimore, Md., Nov. 4-6, 2013, and Sahu et al., "Characterization of Mammary Tumors Using Noninvasive Tactile and Hyperspectral Sensors," IEEE Sensors Journal, Vol. PP, Issue 9, DOI 10.1109/JSEN. 2014. 2323215, May 2014, the present inventor and others showed that combining the tactile imaging with hyperspectral data can characterize tumors more accurately. We obtained tactile data and spectral data from cameras and used a machine classification algorithm to characterize tumors.

Studies have shown that malignant lesions are typically stiffer than benign lesions. A few methods have been proposed for determining the elasticities of tumors. For example, tactile sensors, piezoelectric finger sensor, and elastography. Some of the artificial tactile sensing methods previously proposed use a transduction method to estimate the stress information and obtain elasticity data using a computational model. Commercial palpation imaging systems are available from companies such as Medical Tactile™ Inc. and Assurance Medical™ Inc. These sensors use hundreds of pressure sensors.

Existing spectral imaging sensors acquire multiple spatially co-registered data in many spectral bands; this is a spin-off from NASA's spectral remote sensing technology. Different wavelengths allow the user to obtain different types of information. Recently, spectral cameras are actively being used in medical applications. Near infrared spectral images are used to estimate blood oxygenation levels of a heart. Most spectral systems developed to date are specifically designed for a particular organ such as the brain. Spectral imaging in the near infrared band has also been used in tumor identification for small animals. U.S. Pat. No. 8,320,996 (Panasyuk et al.) has been obtained for hyperspectral imaging for monitoring physiology 2007. Additional information is available in a related paper, S. V. Panasyuk et al., "Medical hyperspectral imaging to facilitate residual tumor identification during surgery," Cancer Biol. Ther., vol. 6, no. 3, pp. 439-446, 2007. Panasyuk et al. used a spectral microscope to facilitate identification of residual breast tumor in a rat. They successfully differentiated different tissue types. However, the field of view of the system was small (3 cm by 6 cm) and the time required to take the image and analyze is significant.

It has previously been proposed to derive the tissue composition of oxyhemoglobin, deoxyhemoglobin, water, and lipids using spectroscopy. The red band absorption is dominated by deoxyhemoglobin (Hb) with a 760 nm peak, oxyhemoglobin ($HbO_2$) with broad band absorption beyond 800 nm, water with a peak at 970 nm, and lipid with a main peak at 930 nm. Moreover, a spectral camera can determine neoangiogenesis (new vessel formation), which is often associated with cancer. Thus, it is possible to correlate the optical properties with physiological parameters. It has been suggested that spectral information can be used to derive physiological conditions of tissue.

Several research groups have demonstrated the sensitivity of spectral markers of breast cancer. For example, in diseased tissue, measurements of tumor total hemoglobin concentration typically are 2-4 fold greater than in normal tissue, and tumor $StO_2$ (tissue oxygen saturation) values are generally reduced by 5-20%. Water content is also a reliable indicator of tumors such as fibroadenomas. The absorption of oxyhemoglobin and deoxyhemoglobin dominates at the shorter wavelengths (600-850 nm) of the spectral window for optical mammography. The absorption of lipid and water are relevant at longer wavelengths (900-1000 nm). Quantification of oxyhemoglobin concentration [$HbO_2$] and deoxyhemoglobin concentration [Hb] in breast tissue allows for measurements of tissue oxygen saturation $StO_2$=[$HbO_2$]/ ([$HbO_2$]+[Hb]) and total hemoglobin concentration [HbT]= [$HbO_2$]+[Hb]. The tumor tissue displays increased absorption (decreased reflectance or absorption) in the 650-850 nm spectral range, corresponding to higher tumor total hemoglobin concentration.

The lipid/water ratio is substantially greater for normal tissue, which corresponds to a significant increase in tumor water content. Also, breast tumor tissue has higher scattering values and a steeper scattering slope than normal tissue. This suggests that tumor is composed of smaller scattering particles compared to the surrounding, principally fatty tissue. Overall, the differences in spectra between the two tissue types (malignant vs. benign) are manifestations of multiple physiological changes due to increased vascularity, cellularity, oxygen consumption and edema in malignant tumor.

There is at the time of writing no commercial system for veterinary mammary tumor screening, but spectroscopy-based devices are available for human breast tumor screening, using static laser-based technologies to assess various optical properties of breast abnormalities. ComfortScan of DOBI Medical International (East Windsor, Conn., http://dobiglobal.com/index.htm) uses a dynamic method that applies uniform pressure and detects the differences of the transilluminations due to angiogenesis (growth of new blood vessels).

There is still room for further improvement in the non-invasive characterization of tumors.

SUMMARY

According to one aspect, a diffuse transmissive monitor, which may be an imager, measures the width of a target inclusion in a turbid medium. A source of light and a light detector are scanned across on opposite sides of the medium containing the target, while remaining parallel to a central axis, to measure the width, and optionally also the position, of the solid target in a direction perpendicular to the central axis. The scan may be repeated in more than one direction to determine the shape of the target.

According to another aspect, a further scan is conducted with one of the source and the detector remaining stationary and the other of the source and the detector rotating about the stationary one. By combining the width of the target as measured by the parallel and rotating scans, simple trigonometry enables the depth of the target within the medium, in a direction parallel to the central axis, to be estimated.

The tactile imaging sensor (TIS) of the above mentioned WO 2012/006431 may be used to obtain an approximate location of the target so that the scan can be efficiently localized. The same camera may then be used as the imager in the TIS and as the sensor for the present scan.

If the detector is a camera or other imaging device, it may be focused to generate an image of the light distribution at an exit surface of the medium. A series of such images may then be generated as the imager scans across the target, and subsequently combined and analyzed.

The source of light may be a laser diode. Because human and animal flesh is a turbid (both diffusive and absorbent) medium, even a laser beam will spread out within the medium. If the medium is assumed to be uniform, the light reaching detector will be a large circular spot, with the intensity of light decreasing away from the center. If the light is occluded by an opaque target inclusion, either a blurred image of the target or a general dimming of the light may be detected, depending on the amount of diffusion and absorption of the light both before and after the light reaches the target. If the target is itself turbid, but has optical properties different from those of the surrounding medium, then a less pronounced dimming, and possibly a different appearance of the blurred image, may be detected.

Mathematical techniques for calculating the propagation of light through a diffusive medium are well known, and given the dimensions and optical properties of the medium and the target, the expected light distribution at the detector can be calculated. Alternatively, given the optical properties of the medium and the target and the light distribution at the detector, the dimensions of the target can be estimated. However, especially for a non-uniform medium such as human or animal flesh, it may be more effective to calibrate the detector empirically using phantom targets of known sizes.

If a single laser diode or other essentially monochromatic source of light is used, then usually only the size and position of the target can be usefully estimated. However, if the color of the light corresponds to a wavelength in which different types of target have significantly different levels of absorption, some spectroscopic indication of the type of target may be obtained. If a light source, or an array of monochromatic light sources, of different colors is used, then spectral or hyperspectral data as discussed above may be obtained, and because the spectral scanning is synchronized with the scanning to estimate the size and position, valuable additional information on the size and position of the area of a specific target type may be derivable.

The elasticity of the target is calculated by estimating the stress and strain over a range of applied forces. That may be done by the methods described in our above-mentioned WO 2012/006431, or by combining the present scanning monitor with a device for applying a suitable compressive stress to the target and observing the strain caused.

In another aspect of a method and apparatus for tumor characterization, light is conducted by total internal reflection (TIR) through a flexible waveguide, which may be the waveguide of the TIS apparatus mentioned above and described in more detail in our earlier WO 2012/006431. One side of the waveguide is pressed against a medium containing an inclusion, which may be flesh containing a tumor or lump, with at least two applied forces. The distortion of the waveguide breaks TIR and produces an image of the inclusion in light escaping from the opposite side of the waveguide. The stress on the inclusion is determined by measuring the applied force. The strain on the inclusion is determined from the distortion of the flexible waveguide. The elastic modulus is determined as the ratio of the change in stress to the change in strain with changing applied force.

The strain may be estimated from the sum of the brightnesses of the pixels of the image of the inclusion. The sum of the brightnesses may bear an approximately linear relationship to the depth of compression (strain) of the flexible waveguide, which is proportional to the strain of the inclusion.

The size of the inclusion may be estimated from the apparent size of the image by a 3D interpolation related to the measured applied force.

The depth of the inclusion below the surface of the medium contacted by the waveguide may be estimated from the minimum applied force at which the image appears.

The strain may be estimated from the sum of the intensities of the illuminated pixels in the image.

A device that can non-invasively identify malignant tumors is useful for both veterinary and human medicine. A harmless, relative simple-to-operate device that is easily accessible by the patients can further increase the malignant tumor detection rate, by increasing the frequency of screening and the number of patients screened. The imager disclosed in the present specification can screen lesions to provide a probability of a specific lesion being malignant. That will allow more patients to make informed decision to seek larger hospitals with the facilities for more advanced diagnosis and, if necessary, treatment.

Dynamic positioning of the light source and detector geometry can significantly increase the performance of the optical dynamic imaging (ODI) system. In one embodiment, the ODI system will consist of a tactile sensor and diffuse spectral sensors.

The dynamic positioning of sensors, which exploit the mechanical and physiological changes in tissues, can significantly increase the performance in characterization of tumors. The ODI System estimates size, depth, elastic modulus (typically Young's modulus and/or shear modulus) and optical properties of embedded objects. The ODI System consists of a tactile imaging sensor (TIS), and a near infrared diffuse spectral imaging system. To obtain the mechanical properties of the target, the region of interest is compressed with a TIS probe, then the light from the probe is scattered and captured by the camera as a tactile image. On the other hand, using a light source and the camera as a detector, we obtain the diffuse spectral images. From these images, we compute the absorption coefficient of the embedded tumor, tumor phantom, or other target. We move the source-detector pair simultaneously and collect optical information. This maneuver is termed "dynamic positioning." The ODI system also provides position and orientation of the light source and the detectors. The combination of the absorption coefficient and tactile data along with location information improves the size, depth, and elastic modulus estimation.

The ODI System can build on the earlier results to obtain physiologic properties while the tissues are dynamically compressed from the surface. Both tactile and spectral information changes can be quantified.

When compression is applied to the lesion, the device will be able to provide an estimate of the hardness of the lesion. This information can be combined with spectral or "color" information of the lesion to provide an improved estimate of a probability of the lesion being malignant. A malignant tumor and a benign tumor exhibit different color changes when compression is applied. Finally, this device is almost completely harmless, and relatively simple to operate. This device could be available in veterinarians' offices or primary care physicians' offices.

The ODI system can give patients and their health care providers the means to decide whether to go for a biopsy or to monitor the lesion over time. Unlike a mammogram, ODI does not involve any ionizing radiation. Instead, ODI discerns tumors based on touch and color information of compressed lesions. This system is non-invasive, portable, non-harmful, near real-time, and relatively painless. Waiting for the results of diagnostic tests generates a lot of anxiety, and the possibility of near real time results can greatly reduce waiting time. Women are likely to find the ODI System more convenient (because it can be provided in more places) and comfortable (no hard plates pressing down). This system can prescreen for breast cancer in a patient-centric paradigm. Early detection of the cancer will not only improve the survival rate of the patients but also decrease the health care costs. ODI can also be used for diagnostic purposes in conjunction with a mammogram.

Potential applications of the disclosed devices include: veterinary mammary tumor detection, spontaneous tumor characterization, breast tumor characterization, breast tumor prescreening, tumor diagnosis, thyroid cancer detection, and skin lesion characterization.

BRIEF DESCRIPTION OF THE DRAWINGS

The following detailed description may be read in conjunction with the accompanying drawings, in which like numerals designate like elements throughout the several views, and in which.

DETAILED DESCRIPTION

Figure 1:
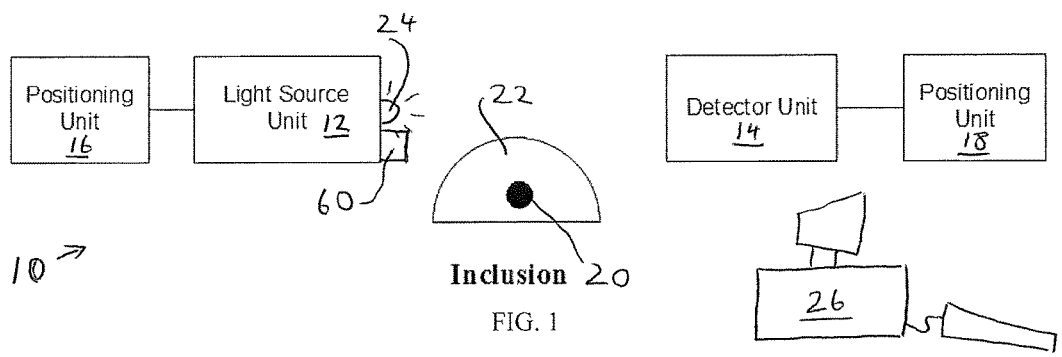
FIG. 1 is a general schematic view of an Optical Dynamic Imaging (ODI) System.

Referring to the drawings, and initially to FIG. 1, one embodiment of an Optical Dynamic Imaging (ODI) system indicated generally by the reference numeral 10 has a light source unit 12, a detector unit 14, and two positioning units 16 and 18, one for the light source unit 12 and one for the detector unit 14. Depending on whether tactile information is to be determined or spectral information is to be determined, different units may be used. The positioning units 16 and 18 provide location and orientation information for the light source unit 12 and the detector unit 14, respectively. The positioning units 16 and 18 may be separate units working in synchrony, or may be parts of a single assembly so that the relative alignment of the light source unit 12 and the detector unit 14 is fixed.

The positioning units 16 and 18 may each, or in combination, comprise a mechanical scanning platform that includes a 2-D linear motion controller and a two-axis gimbal. A suitable gimbal is sold by Newmark Inc., USA. However, this motion can be provided in other ways, such as by a robotic manipulator, or even human arm movement. As will be explained below, the linear motion controller is used for producing controlled parallel motion of the light source 12 and the detector unit 14 along an axis perpendicular to the optical axis joining them. The two-axis gimbal is used to control the angular position of the light source, while keeping the detector unit 14 in a position directly facing the light source 12.

The positioning unit(s) 16, 18 can comprise a location sensor such as an inertial measurement unit, or accelerometers and a gyroscope. That is especially useful if the positioning mechanism does not precisely set the light source 12 and detector unit 14 to predetermined positions.

There are three types of detector unit 14 employed in the ODI System 10. One is a tactile imaging sensor (TIS) based on total internal reflection, as described in the above-mentioned WO 2012/006431. The second is a diffuse transmissive imager. The third is a spectral sensor, which operates in the visible and/or near-infrared spectral region, and may operate by either transmitted or reflected light. As will become apparent, many of the components maybe used by more than one of the three detector units, which renders the overall system 10 more compact, more economical, and easier to use, because there is less switching of components between stages of the detection process. As shown in FIG. 1, the system 10 is positioned for transmissive sensing of a target inclusion 20 in a medium 22. Purely by way of example, the medium 22 may be a human breast, and the inclusion 20 may be a lump or lesion that is suspected of being cancerous. By way of another example, the inclusion 20 and the medium 22 may be an artificial phantom imitating such a lesion.

The detector unit 14 may be based on a camera or smartphone. The light source 24 in the light source unit 12 may be LEDs or laser diodes. For spectral analysis, the light can be used in reflectance or transmittance. For imaging the shape, size, and location of the target, the light is used in transmissive mode.

The ODI system 10 is controlled by a computer 26, which may be a general purpose computer suitably programmed, or a dedicated controller. As is further explained below, it is contemplated that the computer 26 could be an app running on a smartphone, and the built-in camera of the smartphone, with suitable external lenses or other light-directing attachments, could constitute the detector unit 14.

Tactile Imaging Mode

Figures 2, 3:
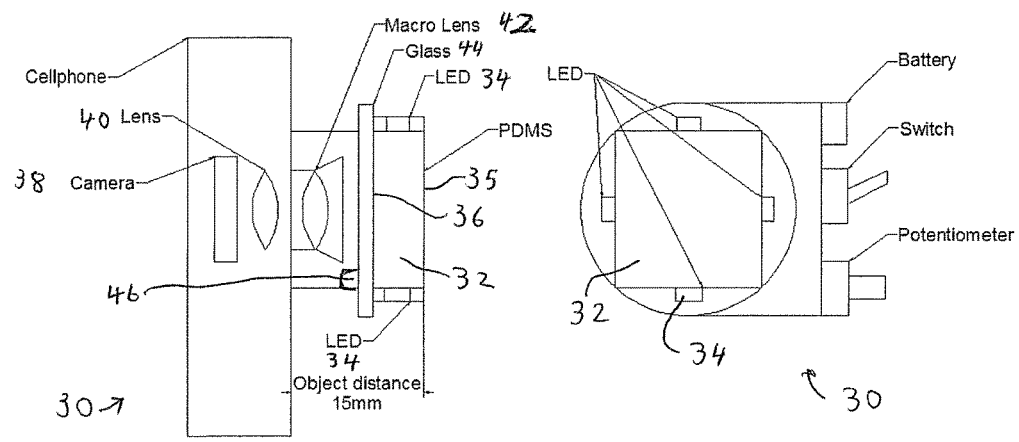
FIG. 2 is a side view of a tactile imaging unit.
FIG. 3 is a front view of the tactile imaging unit of FIG. 2.

Referring to FIGS. 2 and 3, and as described in our above-mentioned WO 2012/006431, the tactile imaging detector unit, indicated generally by the reference numeral 30, which is incorporated in the detector unit 14, has an optical waveguide sensor 32, an array of LEDs 34 that feed light into the sensor. The optical waveguide 32 consists essentially of a flat sheet of flexible transparent material. In a resting state, the light from the LEDs 34 is confined within the optical waveguide 32 by total internal reflection. When the optical waveguide 32 is pressed against the medium 22, the inclusion 20 distorts the front surface 35 of the waveguide 32. That results in light from the LEDs 34 reflecting off the distorted surface 35 at angles that violate the requirement for total internal reflection. That light escapes through the rear face 36 of the optical waveguide 32 in a pattern that forms an image of the distortion, and therefore of the inclusion 20 that caused the distortion. A camera 38 including one or more lenses 40 captures an image of the pattern of light. The separate light source unit 12 is not active in the tactile imaging mode.

The camera 38 may be a conventional camera with the addition of a macro lens 42 to enable it to focus on the rear surface of the optical waveguide 32, which may be only a short distance, for example, 15 mm, from the camera body. The rear face of the optical waveguide 32 may be supported by a substantially rigid glass or hard plastic plate 44 to maintain it at a fixed position on which the camera 38 is focused. A force gauge 46 is provided to measure the force applied to the sensor 32.

In an example, the optical waveguide 32 was made of polydimethylsiloxane (PDMS) which is prepared from component materials RTV 6136-D1 (provided by R. S. Hughes Co., Inc., Sunnyvale, Calif., USA). The sensing probe is flexible, transparent and inert. The sensing area was 23 mm×20 mm. The camera unit consisted of a mono cooled charged-coupled-device (CCD) camera (Guppy F044B-NIR, Allied Vision Technology, Exton, Pa.). The pixel resolution of the sensor was 8.6 μm×8.3 μm. The camera communicated with the computer unit 26 via an IEEE 1394A (Firewire) interface.

The glass plate 36 to provide structural support between the camera and the silicon probe was of heat resistant borosilicate glass. The light source unit consisted of four ultra-bright white light emitting diodes (LEDs). The luminous intensity of each LED was 1500 mcd. The force gauge 46 was from Mark-10 Corporation, Copiague, N.Y., USA. The force gauge has a range of 0 to 50 N with a resolution of $1.0 \times 10^{-3}$ N. A load cell or pressure sensor may be used as an alternative.

As an alternative to the conventional CCD or CMOS camera 38 shown in FIG. 1, the tactile imaging could be done using a smartphone. Mobile devices already have imagers and communication functions. Those functions can be used to implement the above described tactile imaging. The sensor 32, with its LED light source 34, and a suitable macro lens 42, merely need to be attached to the smartphone in front of the built-in camera and lens of the smartphone.

The macro lens 42 can be attached to the mobile device with a magnetic ring. One possible macro lens is made by JEC Technology Ltd, New Zealand. This lens is suitable for any cell phone which has a flat backcover to which a 13 mm diameter ring can be attached. With this lens, the object distance was reduced to 15 mm. Where a conventional camera 38 is used, the camera may be provided with a screw mount in front of an existing lens, or with an interchangeable lens mount, to which a suitable macro lens 42 can be attached.

The force with which the inclusion 20 and the optical waveguide 32 are compressed is an important parameter in mechanical property computation. The force sensor 46 may measure force applied to the medium containing the target directly, or may measure force in a telescoping frame or other resiliently mounted component, or may derive the force from inertial measurements of the movement of the frame.

The main flexible optical waveguide sensor 32 is made of transparent, flexible polymer. One suitable material is a single layer silicone elastomer—Polydimethylsiloxane (PDMS). Another suitable material is polyvinyl chloride (PVC). Alternatively, the optical waveguide sensor 32 can be of multiple layers. However, attention should be paid to the ratio of the refractive indices at the boundaries between layers, and between the rearmost layer of flexible material and the glass plate 44, because that ratio controls the conditions for TIR. One possible set of dimensions of the sensing probe is length, width and thickness of 2.3 cm×2.0 cm×1 cm.

Light sources 34 illuminate the sensing probe 32. Various different light sources 34 can be used. It is presently preferred to use ultra-bright white LEDs, because the color can affect the results of the image. The major function of the LEDs 34 is to provide a full integration of light to illuminate the entire sensing probe. However, as shown in FIG. 3, the LEDs are distributed around the periphery of the optical waveguide 32, one in the center of each edge face of the rectangular block of PDMS 32. Therefore, when the optical waveguide 32 is distorted by the inclusion 20, different sides of the distortion will be illuminated by different ones of the LEDs. The intensity of each individual LED 34 thus affects the pixel values of different parts of the captured image. Therefore, having an equal intensity in each LED 34 and throughout the entire probe 32, or at the very least a consistent and known intensity pattern that can be corrected for in software processing after image capture, is highly desirable.

The number of LEDs 32 on each side of the optical waveguide 32 can be increased in order to increase the area of illumination inside of the waveguide 32.

In addition, or alternatively, each LED 34 could be placed within a white tube, extending along the side of the optical sensor 32 and open towards the optical sensor 32, or other suitable diffusing element, to distribute the light more uniformly within the waveguide 32. Other diffusing transmissive or reflective barriers can be used to supply more uniform light into the sensing probe.

Many types of camera 38, e.g. CCD, CMOS, etc., can be used. Smartphone-based tactile imaging will use the camera installed in the respective smartphone or other mobile device. The camera may capture still images or video. Where video is recorded, the applied force information from the force sensor 46 should be recorded as part of the video stream, possibly in the soundtrack or a synchronized data stream, possibly by providing an output from the force sensor 46 visible at the edge of the field of view of the camera 38. That is desirable because the applied force may vary over time, especially with a hand-held device, and each frame of the video may need to be calibrated according to the force at the time when that frame was captured.

In addition, when measuring the elastic modulus of the target inclusion 20, the pressure is deliberately varied, because determining the difference in stress and difference in strain between two measurements is usually easier than referencing one measurement to a state of zero pressure. Recording video while gradually increasing or decreasing applied force, and then picking out two or more frames from which to calculate the differences, is conceptually simple, but does require synchronized data recording.

A controller 26 with a processor will typically be needed to run the local software of the device 10 that monitors the force sensor 46, takes still and video images, and send them to appropriate operator. The controller 26 can be, for example, a micro-processor, field-programmable gate array (FPGA), computer, laptop, mobile device, etc.

In one smartphone-based example, four 1.5 V batteries were used as a voltage source, and the four LEDs 34 were connected in parallel. Therefore, the voltage across each LED was the same. However, LEDs manufactured in different batches may have difference resistances, so the current drawn by different LEDs, and therefore the light intensity, may be different.

In order to ensure all LEDs are provided with same amount of current, all LEDs are preferably connected in series. In addition, a constant current driver is desirable to stabilize the light output over a range of input voltages, which can increase the life of batteries. Having a constant current driver can also help to avoid damaging the LEDs 34 by exceeding their absolute maximum current rating. Moreover, more predictable and more evenly matched luminous intensity and chromaticity can be obtained by driving all of the LEDs with constant current.

Constant-current drivers for LEDs are well known. One suitable design is based on the LT1932 constant current DC/DC LED Driver of ThinSOT Chip. The LT1932 also supports pulse wave modulation (PWM) to control the brightness of the illumination. In the interests of conciseness, the details of the LED driver will not be described in more detail here.

ODI Method for Size and Depth Estimation

Figure 4:
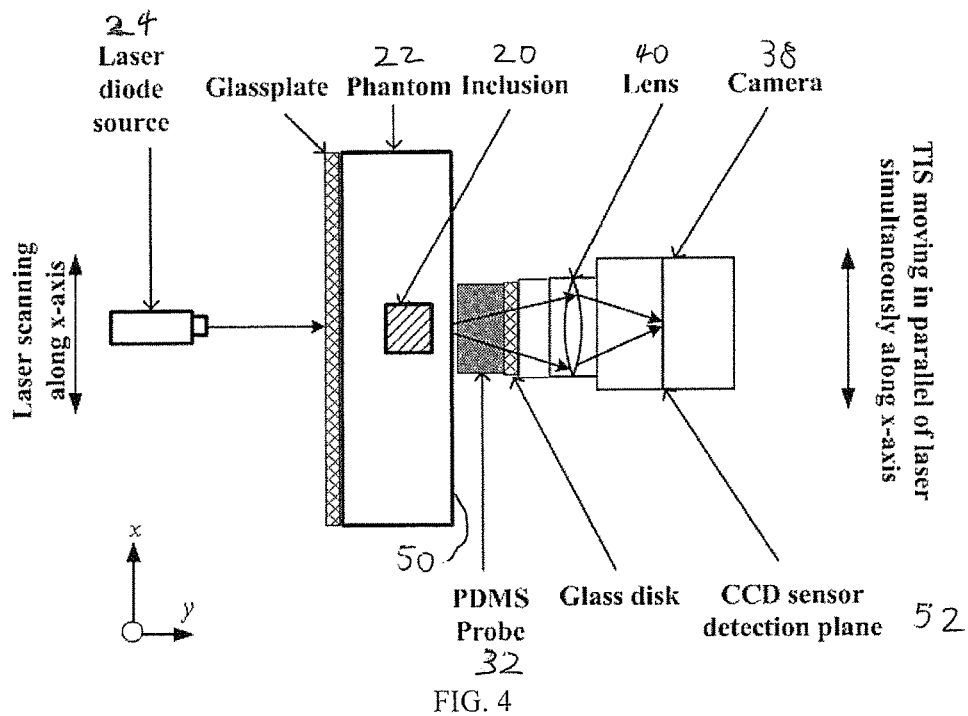
FIG. 4 is a top view of the diffuse imaging subassembly during parallel scanning.
Figure 5:
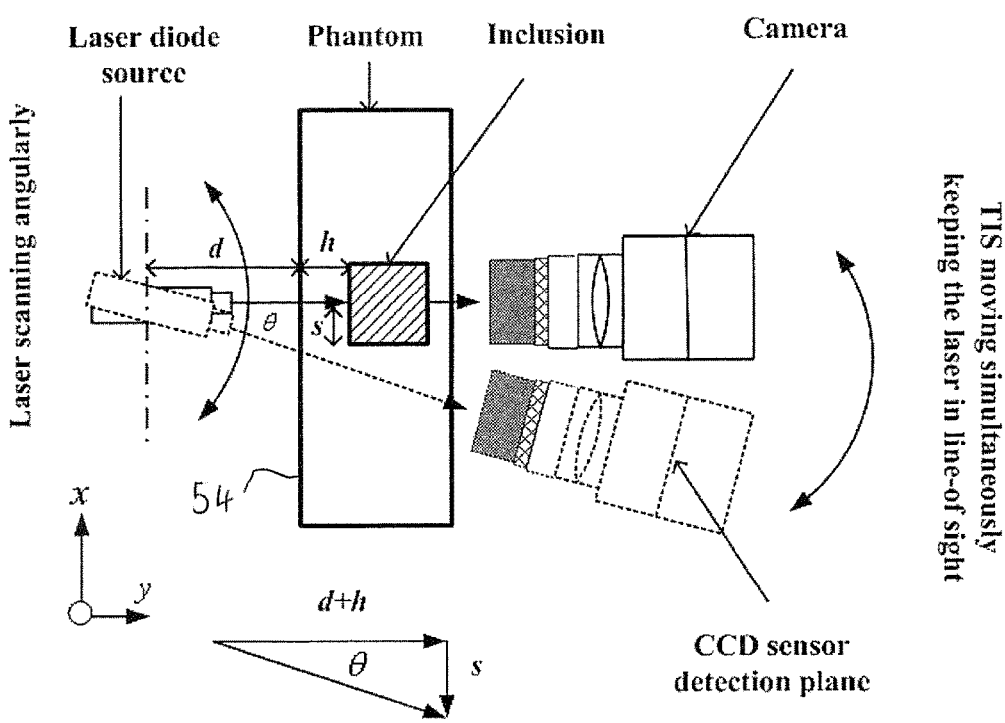
FIG. 5 is a top view of the diffuse imaging subassembly during rotary scanning.

Referring now also to FIGS. 4 and 5, for the Optical Dynamic Imaging (ODI) dynamic positioning method, a near infrared laser diode is used as the light source 24 of FIG. 1. The sensor 32, 38, 40, 42 of FIGS. 2 and 3 may be retained, but the LEDs 34 are switched off. The sensor 32 is moved out of contact with the medium 22, but is not moved sideways, so the position of the inclusion 20 detected by the tactile imaging sensor remains correct relative to the ODI system 10, and can be used as a starting point for the ODI size estimation, reducing the area that has to be scanned. The camera 38 is refocused to image the exit surface 50 of the medium 22 onto the CCD 52 or other image capturing plane of the camera. The laser diode 24 is aimed along the central optical axis (z-axis) of the camera 38.

To carry out ODI, the laser diode 24 and the camera 38 are moved in parallel simultaneously along the x-axis. A stream of images of the exit surface 50 are obtained, which represent diffuse images of the laser diode 24, and of the inclusion 20 silhouetted in front of the light of the laser diode 24. Unless the inclusion 20 is close to the exit surface 50, or the medium 22 is unusually clear, it is typically not expected that any single image from the camera 38 will contain a useful image of the inclusion 20. Typically, only a blurred disk of light, the laser diode 24 diffused by the medium 22, will be seen, and the sum of the pixel intensities is taken as a measure of the total brightness of that image.

However, it is assumed that the inclusion 20 absorbs light more strongly than the surrounding medium 22. Therefore, by analyzing the images, an absorption coefficient Pa is determined for each position of the laser 24. The measured absorption coefficient is expected to be higher when the inclusion 20 is eclipsing the laser 24. Next, a graph of $\mu_a$ versus x is plotted. The inclusion 20 is represented by a region of Pa value higher than that of the medium 22 with small variation, and the edge is represented by a transition from the higher value of $\mu_a$ to the value for the medium 22. This gives us the ODI size estimation. The point within the transition that is deemed to represent the actual edge may be calculated by applying standard mathematical models of light dispersion within a diffusive, absorbent medium, or may be established empirically using specimens with inclusions of known size and properties at a known depth in a turbid medium with known thickness and properties.

The size of the blurred disk of light provides an indication of the scattering coefficient $\mu'_s$. Knowing both $\mu_a$ and $\mu'_s$ provides information about the composition of the turbid medium 22 that may be useful under some circumstances. For example, if $\mu_a$ and $\mu'_s$ are determined at an appropriate wavelength, they may provide chromophore concentration data.

If more information is required, the scan may be repeated, either rotating the scan direction around the z axis within the x-y plane, or with a scan line offset sideways from the original x-axis, or both, to give a fuller picture of the shape, size, and location of the inclusion 20, at least as projected onto the x-y plane.

However, the process illustrated by FIG. 4 gives very little information about the position of the inclusion 20 along the z-axis, that is to say, how deep into the medium 22 the inclusion 20 is. Referring now to FIG. 5, therefore, after the size estimation, the laser 24 is positioned at an initial position in such a way that it points at the embedded object 20 at the half-length point of the object 20. Then, the laser 24 is maneuvered angularly, and the Tactile Imaging Sensor 14 is moved simultaneously, as shown by the curved arrows in FIG. 5, keeping the laser in line with the optical axis of the camera 38. The laser scanning angle θ is measured between the current position of the laser and the initial position of the laser when the laser beam was aimed at the center of the inclusion 20. The value of the scanning angle θ at which the laser 24 is aimed at the edge of the inclusion 20 is identified by the change in absorption coefficient $\mu_a$, as described above.

The distance of the laser rotational axis from the entry surface 54 of the medium 22 is denoted by d. The true depth of the embedded object from the entry surface 54 is denoted by h. The initial position of the laser 24, the edge position of the laser 24, and the half-length s of the embedded object form a triangle. From this triangle, we can write $$\tan\theta = \frac{s}{d+h}. \tag{1}$$

Then, we estimate the depth of embedded object from the entry surface 54 as $$h_{est} = \frac{s}{\tan\theta} - d. \tag{2}$$

In FIGS. 4 and 5, the inclusion 20 is shown as a cube, so both the linear width measurement of FIG. 4 and the angular width measurement of FIG. 5 read the face of the cube nearer to the laser. Therefore, the calculation gives a true measure of the depth h to that face of the cube. If the inclusion 20 is rounded, then the linear width measurement of FIG. 4 reads the diameter of the inclusion, but the angular width measurement of FIG. 5 reads the point at which the laser beam is tangent to the rounded inclusion 20. The result will typically be a depth $h_{est}$ to a position that is slightly in front of the center of the inclusion 20. That is believed to be acceptable for most purposes. If the refractive index of the medium 22 is significantly greater than 1, then it may be expedient to calculate notional positions of d and θ in the optical frame of reference of the medium.

Diffuse Spectral Imaging

For diffuse spectral imaging, the apparatus may be used as shown in FIGS. 4 and 5. This diffuse spectral imaging can use either reflected or transmitted light. If it is desired to measure reflectance, an additional light detector 60 is provided on the entry side, on the light source unit 12 close to the laser diode 24. The light may be provided by one or more laser diodes for example, a near-infrared laser diode or a laser diode of 635 nm (orange). If laser diodes or other monochromatic light sources are used, they are chosen to have wavelengths at which the optical properties (reflectance, transmittance, absorption) of materials that are to be distinguished are different. For example, if attempting to distinguish between cancerous and benign lesions in human breast tissues, the laser wavelengths for a transmissive system may be any or all of 760 nm (deoxyhemoglobin (Hb) red band absorption), 800 nm (oxyhemoglobin (HbO$_2$), which exhibits a groad-band absorption beyond 800 nm), 930 nm (lipid main peak absorption), and 970 nm (water absorption). For canine mammary tissues, the wavelengths may be any or all of 700 nm (Hb), 840 nm (HbO$_2$), 900 nm (lipid), and 970 nm (water). Alternatively, a broad-band light source may be used, and the wavelengths of interest may be extracted at the detector unit 14.

The spectral imaging can be conducted at the same time as the ODI Method for Size and Depth Estimation, or in a separate process. In either case, the two processes may share a laser 24, or may use different wavelengths.

It is known that the color of human or animal tissue changes when pressure is applied for various reasons (most obviously, because pressure can force blood out of superficial blood vessels). Different types of tissue, for example, a malignant tumor and a benign tumor, exhibit different color changes when compression is applied. It is therefore possible to obtain additional diagnostically useful spectroscopic data by carrying out the spectroscopic measurements while applying controlled, or at least measured, pressure. In the apparatus shown in FIG. 4, the positioning unit 18 and force sensor 46 of the TIS system can be used in cooperation with the multi colored laser diode source 24 or white source 12 and the spectrographic camera 38 of the Diffuse Spectral Imaging system. It is thus possible to obtain that additional data with no additional hardware needed, and no reconfiguration of the hardware needed. The additional data can thus be gathered quickly and easily, and is automatically correctly aligned with the data from the TIS, ODI, and other spectroscopic observations. That alignment is important, because if different data are combined that do not in fact relate to the same tissue, an inaccurate assessment may result.

Instead of using a separate camera, it is possible to use a mobile device's camera to obtain spectral information.

Figure 6:
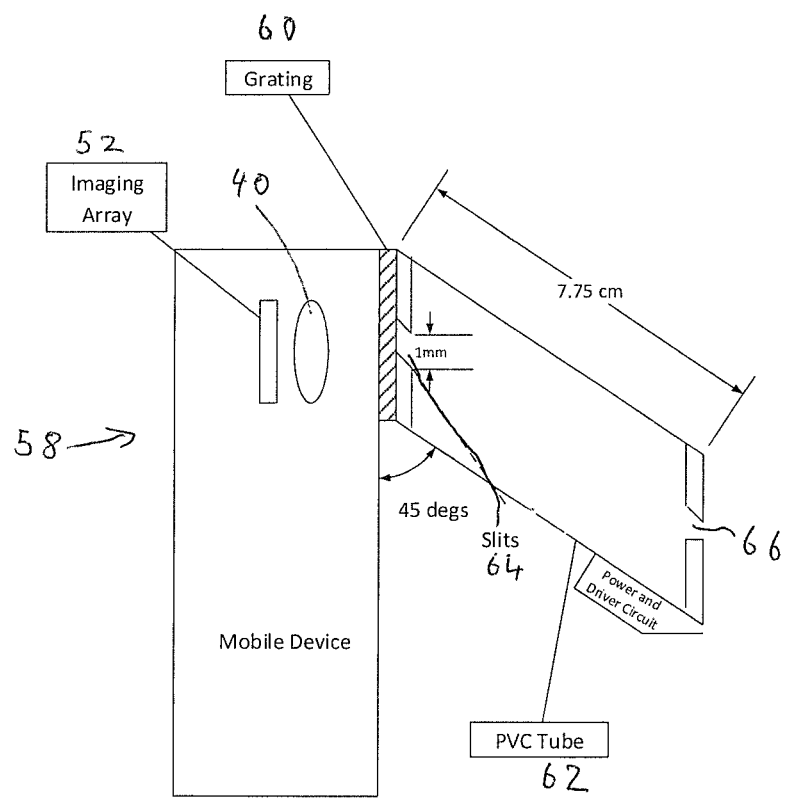
FIG. 6 is a side view of a diffuse spectroscopic detector.

Referring now also to FIG. 6, one embodiment of a spectral imager 58 comprises a diffraction grating 60 in front of the lens 40 of a camera 38, which may be the built-in camera of a smartphone. An opaque tube 62, which in one embodiment was a 7.75 cm long PVC tubing lined with dark foil, was cut in parallel planes at an angle of 45 degrees to the length of the tube at both ends. Parallel slits 64, 66, each 1 mm wide, are formed at the ends of the tube 62. The tube 62 is used to guide incoming light to the diffraction grating at an appropriate angle, so that the spectral lines of interest are diffracted into directions within the field of view of the camera 38, 40, which is a fairly narrow cone centered on an axis perpendicular to the plane of the grating 60. The tube 62 and diffraction grating 60 may be interchanged with the sensor 32, 42 that was used in FIGS. 2 to 5. Preferably, mechanical guides are provided so that the slit 66 at the light inlet end of the tube 62 can be easily and reliably positioned at the same position as the center of the optical waveguide 62.

The spectral detector 58 has the advantage that, because a diffraction grating is used, the differences in color between different spectral lines become differences in position across the imaging array 52. The detector 58 is thus not dependent on the color discrimination of the camera imaging array 52, and can be used with a broadband light source. However, it has the disadvantage that it needs to be interchanged with the probe 32 used in the other embodiments. In contrast, if the probe 32 remains in position, with a typical smartphone camera, useful spectra can only be obtained if a few spectral lines of interest are selected by using laser or other light sources of the correct wavelengths, or by using narrow-band filters.

Size, Depth, and Young's Modulus Estimation Using ODI

A method of estimating the size and depth of an inclusion have been described above with reference to FIGS. 4 and 5. That method may give more precise size and depth measurements than the method about to be described. However, the additional apparatus needed may not always be available, and accurate readings in transmitted light may not be obtainable if the medium 22 is too thick or too opaque.

As was described above with reference to FIGS. 2 and 3, the tactile imaging sensor directly produces an image that represents the inclusion 20 in full size on the flexible waveguide sensor 32. From this, the size of the inclusion can be estimated directly. However, the size of the detected image is typically smaller than the actual inclusion, depending on the applied force. A 3D interpolation model can be used to estimate the actual diameter D of inclusions 20 using tactile data:

$$D(F, N_p) = \sum_{i=0}^{n} \sum_{j=0}^{m} p_{ij} F^i N_p^j \qquad (3)$$

Where F is the applied normal force, $N_p$ is the number of pixels on the compression-induced image, and m and n denote the order of the polynomial.

The significant terms are believed to be:

$$D = p_{00} + p_{10}F + p_{01}N_p + p_{20}F^2 + p_{11}FN_p + p_{30}F^3 + p_{21}F^2N_p \qquad (4)$$

Where the $p_{ij}$ are constants to be determined empirically.

Depth can be estimated from the minimum force required to produce a detectable image in the tactile image sensor, corresponding to the level of distortion of the flexible waveguide 32 that just breaks total internal reflection. This is given as follows:

$$b = \frac{F_{min} - c_1}{c_2}, \qquad (5)$$

where b is depth, $F_{min}$ is the minimum force, $c_1$ and $c_2$ are constants to be determined empirically for a specific apparatus. Alternatively, in many cases the depth can be estimated by the health care provider.

ODI Method for Elastic Modulus Estimation

Elasticity describes the ability of a material to resist being deformed by an applied stress, and to recover its shape after an applied stress is removed. The responses of human skin and soft tissues on compression are examples of elastic tissue recovery. Elastic modulus is used to describe the stiffness of an object. It is defined as the slope of stress-strain curve in the elastic deformation region, which is close to a straight line. The stress is defined as the force per unit area. The strain is defined as the fractional change of size because of stress. However, biological tissues have time dependent elasticity properties. In order to minimize the effects of this time dependency, it is recommended to apply any force with a constant small rate of change. We have found 2 N/s to be satisfactory in our experiments.

To calculate stress $\sigma_z(k)$ on the target inclusion 20 for each tactile image, the following formula is used:

$$\sigma_z(k) = \frac{F(k) - F_{ref}}{A_C}, \tag{6}$$

where $F_k$ are the applied forces, $F_{ref}$ is an initial force value used as a reference, k is the index of applied forces, and $A_c$ is the area of contact between the tactile sensor probe surface and the object being measured. The force $F_k$ may be measured by a force sensor 46, such as a pressure sensor or load cell.

To estimate the strain $\varepsilon_z$ in the vertical (z) direction for each k-th tactile image, the following formula is used:

$$\varepsilon_z(k) = \frac{\Delta L}{L} = \frac{|I(k) - I_{ref}|}{I_{ref}}, \tag{7}$$

Where $\Delta L$ is the change in the height of the target inclusion in the z-direction under applied compression, L is the initial height of the target inclusion, I(k) is the sum of the pixel intensity values of the tactile image captured with k-th force and $I_{ref}$ is the sum of pixel values of tactile image captured at minimum force level, corresponding to $F_{ref}$. The absolute values of $F_{ref}$ and $I_{ref}$ are not important, because if a difference is taken between the values of $\sigma_z$ and $\varepsilon_z$ for two non-zero values of k, then $F_{ref}$ and $I_{ref}$ cancel out.

The intensity sum values can be used for the estimation of the change $\Delta L$ in the z-directional height of the target 20, because the image sum of intensity change is linearly proportional to the height of the indentation into the soft front surface of the flexible waveguide 32. It will be seen that the amount of indentation of the flexible waveguide 32 depends on the actual stiffnesses of the target inclusion 20 and of the material of the flexible waveguide 32, and what is actually measured is a relationship between the stiffnesses of the two. A scaling factor, dependent on the material chosen for the flexible waveguide, may therefore be included in the calculation. Because what is directly measured is the compression of the waveguide material 32, at any given stress a higher $\Delta L$ will correspond to a stiffer inclusion 20 (lower strain), so the scaling factor may have a negative sign.

In a practical situation, the measured force will include force borne by the medium 22, as well as force borne by the target inclusion 20. However, because soft tissue tumors are typically soft in absolute terms, though stiffer than the surrounding flesh, an initially spherical tumor will typically deform under pressure so as to become an oblate spheroid, wider in the x and y directions and shorter in the z direction. The calculation is simplest if the applied pressure can be chosen so that the inclusion 20 just fits the working area of the flexible waveguide 32. That may not be possible if the tumor is too large or too small. However, by multiple measurements at different applied forces, it is possible to separate the two force components, and make at least an estimate of the force applied to the target inclusion that is sufficiently accurate to be usable in distinguishing, for example, benign from malignant tumors in a medium of mammary tissue.

Next, the stress and strain values are plotted. A linear regression curve is estimated for a specific strain range. The slope of this curve returns the elastic modulus value.

As may be apparent from the above description, embodiments of the present apparatus and methods can provide some or all of the following features:

Optical Dynamic Imaging (ODI) System provides mechanical signatures such as size, depth, mobility, and elastic modulus of surface and subsurface objects. Dynamic positioning of the light sources and detectors allow more accurate size and depth estimation of the inclusions.

An Optical Dynamic Imaging (ODI) System provides spectral signatures such as absorption coefficients and scattering coefficients of surface and subsurface objects. Dynamic positioning of the light sources and detectors allow more accurate spectral signature computations.

An ODI System can be used in both reflectance and transillumination mode by dynamically changing the source/detector geometry.

An ODI System can determine the location and orientation and/or detector using a robotic manipulator, inertial sensors, or smartphones.

A linear movement method of tightly integrating tactile and spectral information may provide more accurate target size information than tactile imaging sensing (TIS) alone.

An angular movement method of tightly integrating tactile and spectral information may provide more accurate depth information than TIS alone.

An elastic modulus of the target can be computed from the inclusion size information.

The ODI system uses dynamic positioning of the sensor. The movement of the source/detector pair is described for accurate size and depth information.

The invention claimed is:

1. A diffuse transmissive optical monitor for measuring at least one dimension of a target inclusion in a turbid medium, comprising:
   a light source that in use produces a beam of light along an initial optical axis;
   a light detector positioned facing the beam of light to receive light from the source;
   a positioning unit operative to move the light source and the light detector located on opposite sides of the turbid medium transversely to the initial optical axis while the light beam remains parallel to a central axis through a middle point of the target inclusion;
   wherein the light detector in use detects variations in light received from the light source as the light beam passes across the target inclusion;

the monitor is configured to estimate from the variations a dimension of the target inclusion; and wherein the positioning unit is further operative to rotate the light source and the light detector on opposite sides of the turbid medium containing the target inclusion so that the beam rotates about a center of rotation on the central axis;

the light detector in use detects second variations in light received from the light source as the beam rotates across the target inclusion; and the monitor is configured to estimate from the estimated dimension and the second variations a depth of the target inclusion along the central axis.

2. The monitor of claim 1, wherein the center of rotation is substantially at the light source.

3. The monitor of claim 1, which is further configured to estimate from the variations a position of the target inclusion.

4. The monitor of claim 1, wherein the light source comprises at least one laser diode.

5. The monitor of claim 4, wherein the at least one laser diode comprises a plurality of laser diodes emissive at different wavelengths within the waveband consisting of visible light and near infrared light.

6. The monitor of claim 5, wherein the different wavelengths comprise at least one wavelength selected from the group consisting of: 700 nm, 760 nm, 800 nm, 840 nm, 900 nm, 930 nm, and 970 nm.

7. The monitor of claim 1, which is further configured to derive spectrographic data relating to a composition of at least one of said turbid medium and said target inclusion by detecting at least one of absorption, reflection, and scattering of light of a specific wavelength from said light source.

8. The monitor of claim 1, wherein the light detector is an imaging device operative to image a distribution of light at an exit surface of the turbid medium.

9. The monitor of claim 1, wherein the positioning unit is a robotic manipulator for dynamically locating and orienting the light source unit and the detector unit for determining additional dimensions of the target inclusion.

10. The monitor of claim 9, wherein the robotic manipulator least one inertial measurement unit, an accelerometer, and a gyroscope.

11. The monitor of claim 1, wherein the positioning unit includes an inertial measurement unit for measuring the position and orientation of the sensing device.

12. A diffuse transmissive optical monitor for measuring at least one dimension of a target inclusion in a turbid medium, comprising:

a light source that in use produces a beam of light along an initial optical axis;

a light detector positioned facing the beam of light to receive light from the source;

a positioning unit operative to move the light source and the light detector located on opposite sides of the turbid medium transversely to the initial optical axis while the light beam remains parallel to a central axis through a middle point of the target inclusion;

wherein the light detector in use detects variations in light received from the light source as the light beam passes across the target inclusion;

the monitor is configured to estimate from the variations a dimension of the target inclusion;

further comprising a tactile sensor comprising:

a planar optical waveguide comprising a first layer that is flexible and transparent;

at least one source of illumination configured to direct light into the optical waveguide; and a light sensor facing the optical waveguide and configured to generate signals from light scattered out of the optical waveguide;

wherein the waveguide is configured so that at least some of the light directed into the optical waveguide is scattered out of the first layer when the first layer is deformed, and wherein in use the first layer is deformed by the tactile sensor being pressed against an object.

13. The monitor of claim 12, wherein said light sensor is said light detector.

14. The monitor of claim 12, wherein the positioning unit is a robotic manipulator for dynamically locating and orienting the light source unit and the detector unit for determining additional dimensions of the target inclusion.

15. The monitor of claim 14, wherein the robotic manipulator includes at least one of an inertial measurement unit, an accelerometer, and a gyroscope.

16. The monitor of claim 12, wherein the positioning unit includes an inertial measurement unit for measuring the position and orientation of the sensing device.

17. A method of measuring at least one dimension of a target inclusion in a turbid medium, comprising:

directing a beam of light at the turbid medium along an initial optical axis;

moving the light beam transversely to the initial optical axis while maintaining the light beam parallel to a central axis through a middle point of the target inclusion;

detecting variations in light from the source at an opposite side of the turbid medium as the light beam passes across the target inclusion; and estimating from the variations a dimension of the target inclusion;

rotating the light source so that the beam rotates about a center of rotation on the central axis;

detecting second variations in light received from the light source as the beam rotates across the target inclusion; and estimating from the estimated dimension and the second variations a depth of the target inclusion along the central axis.

18. The method of claim 17, wherein the center of rotation is substantially at a source of the beam of light.

19. The method of claim 17, further comprising estimating from the variations a position of the target inclusion.

20. The method of claim 17, wherein the beam of light comprises at least one laser beam.

21. The method of claim 20, wherein the at least one laser beam comprises laser light of a plurality of different wavelengths within the waveband consisting of visible light and near infrared light.

22. The method of claim 21, wherein the different wavelengths comprise at least one wavelength selected from the group consisting of: 700 nm, 760 nm, 800 nm, 840 nm, 900 nm, 930 nm, and 970 nm.

23. The method of claim 17, further comprising deriving spectrographic data relating to a composition of at least one of said turbid medium and said target inclusion by detecting at least one of absorption, reflection, and scattering of light of a specific wavelength from said light beam.

24. The method of claim 17, wherein the detecting comprises imaging a distribution of light at an exit surface of the turbid medium.

25. A non-transitory computer readable storage medium containing a computer program containing instructions to cause a suitably constructed monitor to carry out the method of claim 17.

26. The method of claim 17, further comprising the step of changing the angular optical axis of the light beam relative to the initial optical axis while maintaining the direction of the light beam toward the target inclusion.

27. The method of claim 17, wherein the step of moving the light beam transversely involves moving the light beam in two or more transverse directions.

28. A method of measuring at least one dimension a of a target inclusion in a turbid medium, comprising:
- directing a beam of light at the turbid medium along an initial optical axis;
- moving the light beam transversely to the initial optical axis while maintaining the light beam parallel to a central axis through a middle point of the target inclusion;
- detecting variations in light from the source at an opposite side of the turbid medium as the light beam passes across the target inclusion; and
- estimating from the variations a width of the target inclusion further comprising:
- directing light into a flexible optical waveguide;
- pressing the optical flexible waveguide onto the turbid medium at a location of the target inclusion;
- generating signals from the directed light that is scattered out of the flexible optical waveguide by the optical flexible waveguide deforming from the pressing; and
- determining from the generated signals a location of the target inclusion.

29. The method of claim 28, further comprising using the determined location of the target inclusion to choose a starting point for the directing of a beam of light at the turbid medium and scanning of the light beam transversely.

30. The method of claim 28, comprising using a common light detector for said detecting of variations and said generating of signals.

31. The method of claim 28, further comprising the step of changing the angular optical axis of the light beam relative to the initial optical axis while maintaining the direction of the light beam toward the target inclusion.

32. The method of claim 28, wherein the step of moving the light beam transversely involves moving the light beam in two or more transverse directions.

* * * * *